(12) United States Patent
Bhagwat et al.

(10) Patent No.: US 9,095,594 B2
(45) Date of Patent: Aug. 4, 2015

(54) PHARMACEUTICAL COMPOSITIONS COMPRISING BETA-LACTAM ANTIBIOTIC, SULBACTAM AND BETA-LACTAMASE INHIBITOR

(75) Inventors: Sachin Subhash Bhagwat, Aurangabad (IN); Mahesh Vithalbhai Patel, Aurangabad (IN)

(73) Assignee: Wockhardt Ltd., Bandra-Kurla Complex, Bandra East, Mumbai (IN)

(*) Notice: Subject to any disclaimer, the term of this patent is extended or adjusted under 35 U.S.C. 154(b) by 0 days.

(21) Appl. No.: 14/114,207

(22) PCT Filed: Oct. 4, 2011

(86) PCT No.: PCT/IB2011/054352
§ 371 (c)(1),
(2), (4) Date: Nov. 21, 2013

(87) PCT Pub. No.: WO2013/014497
PCT Pub. Date: Jan. 31, 2013

(65) Prior Publication Data
US 2014/0213566 A1  Jul. 31, 2014

(30) Foreign Application Priority Data

Jul. 26, 2011 (IN) .......................... 2125/MUM/2011
Jul. 29, 2011 (IN) .......................... 2157/MUM/2011

(51) Int. Cl.
| | | |
|---|---|---|
| A61K 31/00 | (2006.01) |
| A61K 31/546 | (2006.01) |
| A61K 45/06 | (2006.01) |
| A61K 31/4188 | (2006.01) |
| A61K 31/424 | (2006.01) |
| A61K 31/43 | (2006.01) |
| A61K 31/431 | (2006.01) |
| A61K 31/439 | (2006.01) |

(52) U.S. Cl.
CPC ........... *A61K 31/546* (2013.01); *A61K 31/4188* (2013.01); *A61K 31/424* (2013.01); *A61K 31/43* (2013.01); *A61K 31/431* (2013.01); *A61K 31/439* (2013.01); *A61K 45/06* (2013.01)

(58) Field of Classification Search
CPC ........... A61K 2300/00; A61K 31/4188; A61K 31/424; A61K 31/43; A61K 31/431; A61K 31/439; A61K 31/546
USPC .............................................. 514/192, 210.05
See application file for complete search history.

(56) References Cited

U.S. PATENT DOCUMENTS

| | | | |
|---|---|---|---|
| 2006/0159757 A1* | 7/2006 | Payne et al. ................... 424/470 |
| 2009/0275552 A1* | 11/2009 | Patel et al. ................ 514/210.05 |
| 2014/0094447 A1* | 4/2014 | Bhagwat et al. .......... 514/210.05 |

OTHER PUBLICATIONS

Drawz et al., "Three Decades of (Beta)-Lactamase Inhibitors", Jan. 2010, Clinical Microbiology Reviews, vol. 23, No. 1, pp. 160-201.*
Lagace-Wiens et al., "Activity of NXL104 in Combination with (Beta)-Lactams against Genetically Characterized *Escherichia coli* and *Klebsiella pneumoniae* Isolates Producing Class A Extended-Spectrum (Beta)-Lactamases and Class C (Beta)-Lactamases", Published Online on Feb. 28, 2011, Antimicrobial Agents and Chemotherapy, vol. 55, No. 5, pp. 2434-2437.*
John D. Buynak, "(Beta)-Lactamase inhibitors: a review of the patent literature (2010-2013)", Expert Opin. Ther. Patents, vol. 23, No. 11, pp. 1469-1481.*

* cited by examiner

*Primary Examiner* — My-Chau T Tran
(74) *Attorney, Agent, or Firm* — Bio Intellectual Property Services LLC (BIO IPS): O. (Sam) Zaghmout

(57) ABSTRACT

Pharmaceutical compositions and methods for treating or preventing bacterial infections are disclosed. The pharmaceutical compositions typically comprise pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

29 Claims, No Drawings

PHARMACEUTICAL COMPOSITIONS COMPRISING BETA-LACTAM ANTIBIOTIC, SULBACTAM AND BETA-LACTAMASE INHIBITOR

RELATED PATENT APPLICATIONS

This application claims the benefit of Indian Patent Application Nos. 2125/MUM/2011 filed on Jul. 26, 2011, and 2157/MUM/2011 filed on Jul. 29, 2011, the disclosures of which are incorporated herein by reference in their entirety as if fully rewritten herein. All references including patents, patent applications, and literature cited in the specification are expressly incorporated herein by reference in their entirety.

FIELD OF THE INVENTION

The invention relates to antibacterial compositions and methods for preventing or treating bacterial infections.

BACKGROUND OF THE INVENTION

Resistance to beta-lactam antibiotics is wide spread and a key concern. One of the mechanism bacteria have developed against beta-lactam antibiotics is production of several beta-lactamase enzymes, which deactivate the beta-lactam antibiotic. In general, a typical beta-lactam antibiotic alone may not be effective in treating infections caused by such beta-lactamase producing bacteria. One alternative to treating infections caused by bacteria producing beta-lactamase enzymes is by co-administration of a beta-lactamase inhibitor with the beta-lactam antibiotic. The beta-lactamase inhibitor prevents deactivation of a beta-lactam antibiotic, typically by binding with the beta-lactamase enzyme. However, even the combination therapy is also proving ineffective in treating infections caused by newer ESBL strains.

Drawz et al. (Clinical Microbiology Reviews, 2010, 23(1), pages 160-201) have reviewed developments in the area of beta-lactamase inhibition and inhibitors. Drawz et al. summarize various beta-lactamase inhibitors developed to overcome bacterial resistance. Gold et al. (The New England Journal of Medicine, 1996, 335(19), pages 1445-1453) have also reviewed the subject of antimicrobial drug resistance.

The widespread emergence of newer strains that do not respond to even the combination therapies, is becoming a major concern. It is estimated that, internationally the prevalence of ESBL in *Klebsiella* and *E. coli* is in the range of 30-50% depending upon the geographical location. For ESBLs, carbapenem therapy is the most widely used in the clinical settings today. Presently, all strains identified as inhibitor resistant ESBLs are treated only by carbapenems. However, some of the emerging ESBLs (e.g. those containing metallo-betalactamases, KPCs and Class D ESBLs) appear to exhibit higher degree of resistance to even carbapenems. Thus, there is a need to develop new ways to treat infections that are becoming resistant to known therapies and methods.

SUMMARY OF THE INVENTION

Accordingly, there are provided pharmaceutical compositions and methods for treating or preventing bacterial infections.

In one general aspect, there are provided pharmaceutical compositions comprising pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said method comprising administering to said subject a pharmaceutically effective amount of a pharmaceutical composition comprising pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said method comprising administering to said subject a pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said infection being caused by bacteria producing one or more beta-lactamase enzymes, said method comprising administering to said subject a pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for increasing antibiotic effectiveness of a beta-lactam antibiotic in a subject, said method comprising co-administering said beta-lactam antibiotic with a pharmaceutically effective amount of: (a) sulbactam or a pharmaceutically acceptable salt thereof, and (b) at least one beta-lactamase inhibitor or a pharmaceutically acceptable salt thereof, with the provision that the beta-lactamase inhibitor is not sulbactam.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

The inventors have surprisingly discovered that a pharmaceutical composition comprising pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam, exhibits unexpectedly improved antibacterial efficacy, even against highly resistant ESBL producing bacteria.

The term "infection" as used herein includes presence of bacteria, in or on a subject, which, if its growth were inhibited, would result in a benefit to the subject. As such, the term "infection" in addition to referring to the presence of bacteria also refers to normal flora, which are not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. The term "treat", "treating" or "treatment" as used herein also refers to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibiotic or a pharmaceutical composition is the amount of the antibiotic or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibiotic used. For prophylactic treatments, a therapeutically or prophylactically effective amount is that amount which would be effective to prevent a microbial (e.g. bacterial) infection.

The term "administration" or "administering" includes delivery of a composition or one or more pharmaceutically active ingredients to a subject, including for example, by any appropriate methods, which serves to deliver the composition or it's active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition that comprises more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including processes that keep the microorganism alive.

The term, "effectiveness" as used herein refers to ability of a treatment or a composition or one or more pharmaceutically active ingredients to produce a desired biological effect in a subject. For example, the term "antibiotic effectiveness" of a composition or a beta-lactam antibiotic refers to the ability of the composition or the beta-lactam antibiotic to prevent or treat the microbial (e.g. bacterial) infection in a subject.

The term "synergistic" or "synergy" as used herein refers to the interaction of two or more agents so that their combined effect is greater than their individual effects.

The term "antibiotic" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibiotic" also refers to compounds capable of decreasing infectivity or virulence of bacteria.

The term "beta-lactam antibiotic" as used herein refers to compounds with antibiotic properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam antibiotic, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (J. Pharmaceutical Sciences, 66: 1-19 (1977)), incorporated herein by reference, describes various pharmaceutically acceptable salts in details.

The term "Ceftolozane" as used herein refers to a compound also known as CXA-101 (CAS Registry No.: 689293-68-3; Chemical Name: (6R,7R)-3-[(5-amino-4-{[(2-amino-ethyl)carbamoyl]amino}-1-methyl-1H-pyrazol-2-ium-2-yl) methyl]-7-({(2Z)-2-(5-amino-1,2,4-thiadiazol-3-yl)-2-[(1-carboxy-1-methyl ethoxy)imino]acetyl}amino)-8-oxo-5-thia-1-azabicyclo[4.2.0]oct-2-ene-2-carboxylate). A reference to CXA-101 is intended to include its pharmaceutically acceptable salts, pro-drugs, metabolites, esters, ethers, hydrates, polymorphs, solvates, complexes, enantiomers, adducts and its any other pharmaceutically acceptable derivative. CXA-101 has a chemical structure as given Formula (I), below:

Formula (I)

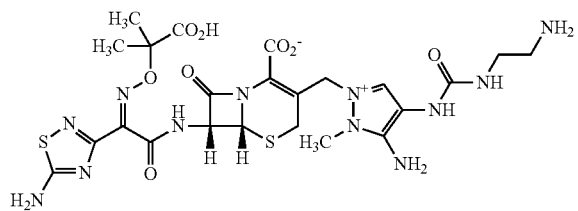

The term "trans-7-oxo-6-(sulphooxy)-1,6-diazabicyclo-[3.2.1]-octane-2-carboxamide" as used herein refers to a compound also known as Sulfuric acid, mono[(1R,2S,5R)-2-(aminocarbonyl)-7-oxo-1,6-diazabicyclo[3.2.1]oct-6-yl]ester). A reference to "trans-7-oxo-6-(sulphooxy)-1,6-diazabicyclo-[3.2.1]-octane-2-carboxamide" is intended to include its pharmaceutically acceptable salts, pro-drugs, metabolites, esters, ethers, hydrates, polymorphs, solvates, complexes, enantiomers, adducts and its any other pharmaceutically acceptable derivative.

A person of skills in the art would appreciate that various compounds described herein (including, for example, the beta-lactam antibiotic; sulbactam; and the beta-lactamase inhibitor) can exist and are often used as their pharmaceutically acceptable salts, pro-drugs, metabolites, esters, ethers, hydrates, polymorphs, solvates, complexes, enantiomers, adducts and other pharmaceutically acceptable derivatives. A reference to compounds discussed herein, therefore, is intended to include such pharmaceutically acceptable salts, pro-drugs, metabolites, esters, ethers, hydrates, polymorphs, solvates, complexes, enantiomers, adducts and their any other pharmaceutically acceptable derivatives. For example, the terms "beta-lactam antibiotic", "sulbactam", and "beta-lactamase inhibitor" includes their pharmaceutically acceptable salts, pro-drugs, metabolites, esters, ethers, hydrates, polymorphs, solvates, complexes, enantiomers, adducts and their any other pharmaceutically acceptable derivatives.

In one general aspect, there are provided pharmaceutical compositions comprising pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said method comprising administering to said subject a pharmaceutically effective amount of a pharmaceutical composition comprising pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said method comprising administering to said subject a pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for preventing or treating a bacterial infection in a subject, said infection being caused by bacteria producing one or more beta-lactamase enzymes, said method comprising administering to said subject a pharmaceutically effective amount of: (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam.

In another general aspect, there is provided a method for increasing antibiotic effectiveness of a beta-lactam antibiotic in a subject, said method comprising co-administering said beta-lactam antibiotic with a pharmaceutically effective amount of: (a) sulbactam or a pharmaceutically acceptable salt thereof, and (b) at least one beta-lactamase inhibitor or a pharmaceutically acceptable salt thereof, with the provision that the beta-lactamase inhibitor is not sulbactam.

The compositions and methods according to this invention use a beta-lactam antibiotic. In general, any beta-lactam antibiotic (a beta-lactam antibiotic is a compound with antibiotic properties and contains a beta-lactam nucleus in its molecular structure) could be used in compositions and methods according to this invention. If desired, a suitable derivative of a beta-lactam antibiotic may also be used. Non-limiting examples of suitable derivatives include pro-drugs, metabolites, esters, ethers, hydrates, polymorphs, solvates, complexes, enantiomers, adducts and a like of such beta-lactam antibiotics. Non-limiting examples of typical beta-lactam antibiotics include those belonging to penicillins, penems, carbapenems, cephalosporins, and monobactams. Typical examples of beta-lactam antibiotics include, but are not limited to amoxicillin, ampicillin, pivampicillin, hetacillin, bacampicillin, metampicillin, talampicillin, epicillin, carbenicillin, ticarcillin, temocillin, azlocillin, piperacillin, mezlocillin, mecillinam, sulbenicillin, clometocillin, benzathine, benzylpenicillin, procaine benzylpenicillin, azidocillin, penamecillin, propicillin, benzathine phenoxymethylpenicillin, pheneticillin, cloxacillin, dicloxacillin, flucloxacillin, oxacillin, methicillin, nafcillin, faropenem, biapenem, ertapenem, doripenem, imipenem, meropenem, panipenem, cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, cephamycin, cefoxitin, cefotetan, cefmetazole, carbacephem, loracarbef, cefixime, ceftriaxone, ceftazidime, cefoperazone, cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, oxacephem, flomoxef, latamoxef, cefepime, cefozopran, cefpirome, cefquinome, ceftobiprole, ceftaroline fosamil, ceftiofur, cefquinome, cefovecin, aztreonam, tigemonam, carumonam, tabtoxin, ceftolozane and the like.

The compositions and methods according to this invention also use sulbactam or pharmaceutically acceptable salts thereof. If desired, a suitable derivative of sulbactam may also be used. Non-limiting examples of such suitable derivatives include pro-drugs, metabolites, esters, ethers, hydrates, polymorphs, solvates, complexes, enantiomers, adducts and a like.

The compositions and methods according to this invention also use one or more beta-lactamase inhibitors or a pharmaceutically acceptable salt. If desired, a suitable derivative of beta-lactamase inhibitor may also be used. Non-limiting examples of suitable derivatives include pro-drugs, metabolites, esters, ethers, hydrates, polymorphs, solvates, complexes, enantiomers, adducts and a like of such beta-lactamase inhibitors. In general, any compound capable of inhibiting activity of one or more beta-lactamase enzymes, either partially or completely, can be advantageously used in the compositions and methods according to this invention.

In some embodiments, the beta-lactam antibiotic in the composition and/or methods according to the invention is selected from the group consisting of penicillins, penems, carbapenems, cephalosporins, and monobactams.

In some other embodiments, the beta-lactam antibiotic in the composition and/or methods according to the invention is a cephalosporin antibiotic selected from the group consisting of cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, ceftaroline, and latamoxef.

In some other embodiments, the beta-lactam antibiotic in the composition and/or methods according to the invention is selected from the group consisting of ceftazidime, cefepime, cefpirome, piperacillin doripenem, meropenem, imipenem, ceftaroline and ceftolozane.

In some embodiments, sulbactam in the composition and/or methods according to the invention is present as sulbactam sodium.

In some embodiments, the beta-lactamase inhibitor in the composition and/or methods according to the invention is at least one selected from tazobactam, clavulanic acid and trans-7-oxo-6-(sulphooxy)-1,6-diazabicyclo-[3.2.1]-octane-2-carboxamide, or a pharmaceutically acceptable salt thereof.

In some other embodiments, the beta-lactamase inhibitor in the composition and/or methods according to the invention is trans-7-oxo-6-(sulphooxy)-1,6-diazabicyclo-[3.2.1]-octane-2-carboxamide, or a pharmaceutically acceptable salt thereof.

In some other embodiments, the beta-lactamase inhibitor in the composition and/or methods according to the invention is sodium salt of trans-7-oxo-6-(sulphooxy)-1,6-diazabicyclo-[3.2.1]-octane-2-carboxamide.

The pharmaceutical compositions according to this invention can exist in various forms. In some embodiments, the pharmaceutical composition is in the form of a powder or a solution.

In some embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for parenteral administration.

The amount of a beta-lactam antibiotic, sulbactam and beta-lactamase inhibitor in the composition may vary depending on specific requirements. In some embodiments, beta-lactam antibiotic is present in the composition in an amount from about 0.01 to about 10 gm. In some other embodiments, sulbactam is present in the composition in an amount from about 0.01 to about 10 gm. In some embodiments, beta-lactamase inhibitor is present in the composition in an amount from about 0.01 to about 10 gm. Amounts below or above these ranges may also be employed, if desired.

In the methods according to the invention, the amount of a beta-lactam antibiotic, sulbactam and beta-lactamase inhibitor that may be administered to a subject may vary depending on specific requirements. In some embodiments, beta-lactam antibiotic is administered in an amount from about 0.01 to about 10 gm per day. In some other embodiments, sulbactam is administered in an amount from about 0.01 to about 10 gm per day. In some embodiments, a beta-lactamase inhibitor is administered in an amount from about 0.01 to about 10 gm per day. Amounts below or above these ranges may also be administered, if desired.

In the methods according to the invention, the pharmaceutical composition and/or other pharmaceutically active ingredients (including, for example, one or more of a beta-lactam antibiotic, sulbactam and beta-lactamase inhibitor) may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients (e.g. beta-lactam antibiotic, sulbactam and beta-lactamase inhibitor) may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients (including, for example, one or more of a beta-lactam antibiotic, sulbactam and beta-lactamase inhibitor) may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) ore are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered be less or not susceptible to one or more of known beta-lactam antibiotic or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compositions and methods according to the invention are also effective in preventing or treating bacterial infections that are caused by bacteria producing one or more beta-lactamase enzymes. The ability of compositions and methods according to the present invention to treat such resistant bacteria with typical beta-lactam antibiotics represents a significant improvement in the art.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

The efficacy of compositions and methods in treating bacterial infections was studied. In a typical study, overnight grown bacterial cultures were diluted appropriately and inoculated on the agar media containing doubling dilutions of the antibiotic. Observation for growth or no growth was performed after 16-20 hours of incubation at 35±2° C. in ambient air. The overall procedure was performed as per Clinical and Laboratory Standards Institute (CLSI) recommendations (Clinical and Laboratory Standards Institute (CLSI), performance Standards for Antimicrobial Susceptibility Testing, 20th Informational Supplement, M 100-S20, Volume 30, No. 1, 2010). The results of these studies are summarized in Tables 1-4.

Table 1 details results of the activity study using cefepime (a beta-lactam antibiotic), sulbactam and NXL-104 (a beta-lactamase inhibitor), alone and in combination with each other. NXL-104 is sodium salt of trans-7-oxo-6-(sulphooxy)-1,6-diazabicyclo-[3.2.1]-octane-2-carboxamide. As can be seen from the data given in Table 1, each of cefepime, sulbactam and NXL-104 have much higher MIC values indicating their lower antibiotic effectiveness, when used alone. A combination comprising any two of cefepime, sulbactam and NXL-104 showed moderate enhancement in the antibiotic effectiveness as compared when these were used alone. However, the MIC values of this double combination are quite higher suggesting that these combinations do not offer substantial improvement in the antibiotic effectiveness. Table 2 details results of the activity studies using a combination of cefepime (a beta-lactam antibiotic), sulbactam and NXL-104 (a beta-lactamase inhibitor). As can be seen, the overall MIC values for cefepime in presence of sulbactam and NXL-104 are surprisingly dropped to as low as less than 0.03 mcg/ml. These finding are even more unexpected since the bacterial strains employed in this study are typically classified as ESBL strains with very high degree of resistance to beta-lactam antibiotic including carbapenems (also confirmed by the cefepime and cefpirome MIC values given in Table 1 and 3). Thus the combinations according to the invention exhibit surprisingly enhanced antibiotic activity.

In view of the data provided in Table 1 and 2, it can be seen that, unexpectedly, a combination comprising (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam, can be effectively used in preventing or treating a bacterial infection (even those being caused by bacteria producing one or more beta-lactamase enzymes) in a subject.

These results also suggest that the antibiotic effectiveness of a beta-lactam antibiotic in a subject can be increased by co-administering said beta-lactam antibiotic with a pharmaceutically effective amount of: (a) sulbactam or a pharmaceutically acceptable salt thereof, and (b) at least one beta-lactamase inhibitor or a pharmaceutically acceptable salt thereof, with the provision that the beta-lactamase inhibitor is not sulbactam. As can be seen, the MIC value for cefepime in this study dropped to as low as 0.03 mcg/ml in presence of sulbactam and NXL-104.

TABLE 2

Activity of cefepime in combination with sulbactam and NXL-104 *

| | | MIC of cefepime (mcg/ml) | | | |
| --- | --- | --- | --- | --- | --- |
| Sr. | ESBL Strain | NXL-104 (4 mcg/ml) + Sulbactam (4 mcg/ml) | NXL-104 (4 mcg/ml) + Sulbactam (8 mcg/ml) | NXL-104 (6 mcg/ml) + Sulbactam (6 mcg/ml) | NXL-104 (8 mcg/ml) + Sulbactam (4 mcg/ml) |
| 1. | A. baumanii 13301 | <0.06 | <0.06 | <0.06 | <0.06 |
| 2. | A. baumanii 13304 | <0.06 | <0.06 | <0.06 | <0.06 |
| 3. | A. baumanii 13305 | <0.06 | <0.06 | <0.06 | <0.06 |
| 4. | A. baumanii S-3 | 16 | 4 | 1 | 0.5 |
| 5. | A. baumanii S-4 | 16 | 4 | 1 | 0.5 |
| 6. | A. baumanii S-8 | 16 | 8 | 0.5 | 0.5 |
| 7. | A. baumanii S-10 | 16 | 8 | <0.03 | <0.03 |

TABLE 1

Activity of cefepime, sulbactam and NXL-104 (alone and in combination with each others)

| | | | | | MIC of cefepime (mcg/ml) | | MIC (mcg/ml) of NXL-104 |
| --- | --- | --- | --- | --- | --- | --- | --- |
| | | | | | In presence of Sulbactam | In presence of NXL-104 | in presence of Sulbactam |
| Sr. | ESBL Strain | Cefepime | Sulbactam | NXL-104 | (4 to 8 mcg/ml) | (4 to 8 mcg/ml) | (4 mcg/ml) |
| 1. | A. baumanii 13301 | >32 | >32 | >64 | >32 | >32 | 2 |
| 2. | A. baumanii 13304 | >32 | >32 | >64 | >32 | 16 | 2 |
| 3. | A. baumanii 13305 | 16 | 16 | >64 | 4 | 16 | 2 |
| 4. | A. baumanii S-3 | >32 | >32 | >64 | >32 | 32 | 16 |
| 5. | A. baumanii S-4 | >32 | >32 | >64 | >32 | 32 | 16 |
| 6. | A. baumanii S-8 | 32 | >32 | >64 | 32 | 16 | 16 |
| 7. | A. baumanii S-10 | >32 | >32 | >64 | >32 | 16 | 16 |
| 8. | A. baumanii S-15 | >32 | >32 | >64 | >32 | 16 | 16 |

TABLE 2-continued

Activity of cefepime in combination with sulbactam and NXL-104 *

| | | MIC of cefepime (mcg/ml) | | | |
|---|---|---|---|---|---|
| Sr. | ESBL Strain | NXL-104 (4 mcg/ml) + Sulbactam (4 mcg/ml) | NXL-104 (4 mcg/ml) + Sulbactam (8 mcg/ml) | NXL-104 (6 mcg/ml) + Sulbactam (6 mcg/ml) | NXL-104 (8 mcg/ml) + Sulbactam (4 mcg/ml) |
| 8. | *A. baumanii* S-15 | 16 | 8 | 0.12 | 0.5 |

* for stand alone MIC values of cefepime, sulbactam and NXL-104, refer Table 1.

Example 2

The efficacy of compositions and methods in treating bacterial infections was studied. The study protocol was same as used in Example 1, except that beta-lactam antibiotic was cefpirome in place of cefepime.

Table 3 details results of the activity study using cefpirome (a beta-lactam antibiotic), sulbactam and NXL-104 (a beta-lactamase inhibitor), alone and in combination with each other. NXL-104 is sodium salt of trans-7-oxo-6-(sulphooxy)-1,6-diazabicyclo-[3.2.1]-octane-2-carboxamide. As can be seen from the data given in Table 1, each of cefpirome, sulbactam and NXL-104 have much higher MIC values indicating their lower antibiotic effectiveness, when used alone. A combination comprising any two of cefpirome, sulbactam and NXL-104 showed moderate enhancement in the antibiotic effectiveness as compared when these were used alone. However, the MIC values of this double combination are quite higher suggesting that these combinations do not offer substantial improvement in the antibiotic effectiveness. Table 4 details results of the activity studies using a combination of cefpirome (a beta-lactam antibiotic), sulbactam and NXL-104 (a beta-lactamase inhibitor). As can be seen, the overall MIC values for cefpirome in presence of sulbactam and NXL-104 are surprisingly dropped to as low as less than 0.03 mcg/ml. These finding are even more unexpected since the bacterial strains employed in this study are typically classified as ESBL strains with very high degree of resistance to beta-lactam antibiotic agents including carbapenems (also confirmed by the cefepime and cefpirome MIC values given in Table 1 and 3). Thus the combinations according to the invention exhibit surprisingly enhanced antibiotic activity.

In view of the data provided in Tables 1-4, it can be seen that, unexpectedly, a combination comprising (a) at least one beta-lactam antibiotic or a pharmaceutically acceptable salt thereof, (b) sulbactam or a pharmaceutically acceptable salt thereof, and (c) at least one beta-lactamase inhibitor or a pharmaceutically acceptable salt thereof, with the provision that the beta-lactamase inhibitor is not sulbactam, can be effectively used in preventing or treating a bacterial infection (even those being caused by bacteria producing one or more beta-lactamase enzymes) in a subject.

TABLE 3

Activity of cefpirome, sulbactam and NXL-104 (alone and in combination with each others)

| | | MIC (mcg/ml) | | | MIC of cefpirome (mcg/ml) | | MIC (mcg/ml) of NXL-104 |
|---|---|---|---|---|---|---|---|
| | | | | | In presence of Sulbactam | In presence of NXL-104 | in presence of Sulbactam |
| Sr. | ESBL Strain | Cefpirome | Sulbactam | NXL-104 | (4 to 8 mcg/ml) | (4 to 8 mcg/ml) | (4 mcg/ml) |
| 1. | *A. baumanii* 13301 | >32 | >32 | >64 | >32 | >32 | 2 |
| 2. | *A. baumanii* 13304 | 32 | >32 | >64 | 32 | 16 | 2 |
| 3. | *A. baumanii* 13305 | 16 | 16 | >64 | 8 | 16 | 2 |
| 4. | *A. baumanii* S-3 | >32 | >32 | >64 | >32 | 32 | 16 |
| 5. | *A. baumanii* S-4 | >32 | >32 | >64 | >32 | 32 | 16 |
| 6. | *A. baumanii* S-8 | 32 | >32 | >64 | 32 | 16 | 16 |
| 7. | *A. baumanii* S-10 | >32 | >32 | >64 | >32 | 16 | 16 |
| 8. | *A. baumanii* S-15 | 32 | >32 | >64 | 32 | 16 | 16 |

TABLE 4

Activity of cefpirome in combination with sulbactam and NXL-104*

| | | MIC of cefpirome (mcg/ml) | | | |
|---|---|---|---|---|---|
| Sr. | ESBL Strain | NXL-104 (4 mcg/ml) + Sulbactam (4 mcg/ml) | NXL-104 (4 mcg/ml) + Sulbactam (8 mcg/ml) | NXL-104 (6 mcg/ml) + Sulbactam (6 mcg/ml) | NXL-104 (8 mcg/ml) + Sulbactam (4 mcg/ml) |
| 1. | *A. baumanii* 13301 | <0.06 | <0.06 | <0.06 | <0.06 |
| 2. | *A. baumanii* 13304 | <0.06 | <0.06 | <0.06 | <0.06 |
| 3. | *A. baumanii* 13305 | <0.06 | <0.06 | <0.06 | <0.06 |
| 4. | *A. baumanii* S-3 | 16 | 4 | 1 | 0.5 |

TABLE 4-continued

Activity of cefpirome in combination with sulbactam and NXL-104*

| | | MIC of cefpirome (mcg/ml) | | | |
|---|---|---|---|---|---|
| Sr. | ESBL Strain | NXL-104 (4 mcg/ml) + Sulbactam (4 mcg/ml) | NXL-104 (4 mcg/ml) + Sulbactam (8 mcg/ml) | NXL-104 (6 mcg/ml) + Sulbactam (6 mcg/ml) | NXL-104 (8 mcg/ml) + Sulbactam (4 mcg/ml) |
| 5. | A. baumanii S-4 | 16 | 4 | 1 | 0.5 |
| 6. | A. baumanii S-8 | 16 | 8 | 0.5 | 0.5 |
| 7. | A. baumanii S-10 | 16 | 8 | <0.03 | <0.03 |
| 8. | A. baumanii S-15 | 16 | 8 | 0.12 | 0.5 |

*for stand alone MIC values of cefpirome, sulbactam and NXL-104, refer Table 3.

The invention claimed is:

1. A pharmaceutical composition comprising pharmaceutically effective amount of: (a) at least one beta-lactam antibiotic or a pharmaceutically acceptable salt thereof, (b) sulbactam or a pharmaceutically acceptable salt thereof, and (c) trans-7-oxo-6-(sulphooxy)-1,6-diazabicyclo-[3.2.1]-octane-2-carboxamide or a pharmaceutically acceptable salt thereof.

2. A pharmaceutical composition according to claim 1, wherein the composition is in the form of a powder or a solution.

3. A pharmaceutical composition according to claim 1, wherein the beta-lactam antibiotic or a pharmaceutically acceptable salt thereof is present in an amount from about 0.01 to about 10 gm.

4. A pharmaceutical composition according to claim 1, wherein sulbactam or a pharmaceutically acceptable salt thereof is present in an amount from about 0.01 to about 10 gm.

5. A pharmaceutical composition according to claim 1, wherein trans-7-oxo-6-(sulphooxy)-1,6-diazabicyclo-[3.2.1]-octane-2-carboxamide or a pharmaceutically acceptable salt thereof is present in an amount from about 0.01 to about 10 gm.

6. A method for treating a bacterial infection in a subject, said method comprising administering to said subject a pharmaceutically effective amount of a pharmaceutical composition according claim 1.

7. A method for treating a bacterial infection in a subject, said infection being caused by bacteria producing one or more beta-lactamase enzymes, wherein the method comprises administering to said subject a pharmaceutically effective amount of a pharmaceutical composition according to claim 1.

8. A pharmaceutical composition according to claim 1, wherein the composition is formulated into a dosage form such that the beta-lactam antibiotic or a pharmaceutically acceptable salt thereof, sulbactam or a pharmaceutically acceptable salt thereof, and trans-7-oxo-6-(sulphooxy)-1,6-diazabicyclo-[3.2.1]-octane-2-carboxamide or a pharmaceutically acceptable salt thereof, are present in the composition as admixture or as separate components.

9. A pharmaceutical composition according to claim 1, wherein the composition is in the form of a powder that can be reconstituted by addition of a compatible reconstitution diluent prior to parenteral administration.

10. A pharmaceutical composition according to claim 1, wherein the composition is in the form of a frozen composition that can be diluted with a compatible diluent prior to parenteral administration.

11. A pharmaceutical composition according to claim 1, wherein the composition is in a form ready to use for parenteral administration.

12. A method for treating a bacterial infection in a subject, said method comprising administering to said subject a pharmaceutically effective amount of: (a) at least one beta-lactam antibiotic or a pharmaceutically acceptable salt thereof, (b) sulbactam or a pharmaceutically acceptable salt thereof, and (c) trans-7-oxo-6-(sulphooxy)-1,6-diazabicyclo-[3.2.1]-octane-2-carboxamide or a pharmaceutically acceptable salt thereof.

13. A method for treating a bacterial infection in a subject, said infection being caused by bacteria producing one or more beta-lactamase enzymes, said method comprising administering to said subject a pharmaceutically effective amount of: (a) at least one beta-lactam antibiotic or a pharmaceutically acceptable salt thereof, (b) sulbactam or a pharmaceutically acceptable salt thereof, and (c) trans-7-oxo-6-(sulphooxy)-1,6-diazabicyclo-[3.2.1]-octane-2-carboxamide or a pharmaceutically acceptable salt thereof.

14. A method for increasing antibiotic effectiveness of a beta-lactam antibiotic in a subject, said method comprising co-administering said beta-lactam antibiotic with a pharmaceutically effective amount of: (a) sulbactam or a pharmaceutically acceptable salt thereof, and (b) trans-7-oxo-6-(sulphooxy)-1,6-diazabicyclo-[3.2.1]-octane-2-carboxamide or a pharmaceutically acceptable salt thereof.

15. A pharmaceutical composition according to any one of claim 1-5 or 8-11, wherein said beta-lactam antibiotic is selected from the group consisting of penicillins, penems, carbapenems, cephalosporins, and monobactams.

16. A pharmaceutical composition according to claim 15, wherein the beta-lactam antibiotic is a cephalosporin antibiotic selected from the group consisting of cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, ceftaroline and latamoxef.

17. A pharmaceutical composition according to claim 15, wherein the beta-lactam antibiotic is selected from the group consisting of ceftazidime, cefepime, cefpirome, piperacillin doripenem, meropenem, imipenem, ceftaroline and ceftolozane.

18. A pharmaceutical composition according to claim 15, wherein sulbactam is present as sulbactam sodium.

19. A pharmaceutical composition according to claim 15, wherein trans-7-oxo-6-(sulphooxy)-1,6-diazabicyclo-[3.2.1]-octane-2-carboxamide is present as a sodium salt of trans-7-oxo-6-(sulphooxy)-1,6-diazabicyclo-[3.2.1]-octane-2-carboxamide.

20. A method according to any one of claims 12 to 14, wherein the beta-lactam antibiotic or a pharmaceutically acceptable salt thereof, sulbactam or a pharmaceutically acceptable salt thereof, and trans-7-oxo-6-(sulphooxy)-1,6- diazabicyclo-[3,2,1]-octane-2-carboxamide or a pharmaceutically acceptable salt thereof are administered separately or as a combined dosage form.

21. A method according to claim 20, wherein said beta-lactam antibiotic is selected from the group consisting of penicillins, penems, carbapenems, cephalosporins, and monobactams.

22. A method according to claim 20, wherein the beta-lactam antibiotic is a cephalosporin antibiotic selected from the group consisting of cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, ceftaroline and latamoxef.

23. A method according to claim 20, wherein the beta-lactam antibiotic is selected from the group consisting of ceftazidime, cefepime, cefpirome, piperacillin doripenem, meropenem, imipenem, ceftaroline and ceftolozane.

24. A method according to claim 20, wherein sulbactam is present as sulbactam sodium.

25. A method according to claim 20, wherein trans-7-oxo-6-(sulphooxy)-1,6-diazabicyclo-[3.2.1]-octane-2-carboxamide is present as a sodium salt of trans-7-oxo-6-(sulphooxy)-1,6-diazabicyclo-[3.2.1]-octane-2-carboxamide.

26. A pharmaceutical composition comprising pharmaceutically effective amount of: (a) cefepime or a pharmaceutically acceptable salt thereof, (b) sulbactam or a pharmaceutically acceptable salt thereof, and (c) trans-7-oxo-6-(sulphooxy)-1,6-diazabicyclo-[3.2.1]-octane-2-carboxamide or a pharmaceutically acceptable salt thereof.

27. A pharmaceutical composition comprising pharmaceutically effective amount of: (a) cefpirome or a pharmaceutically acceptable salt thereof, (b) sulbactam or a pharmaceutically acceptable salt thereof, and (c) trans-7-oxo-6-(sulphooxy)-1,6-diazabicyclo-[3.2.1]-octane-2-carboxamide or a pharmaceutically acceptable salt thereof.

28. A method for treating a bacterial infection in a subject, said method comprising administering to said subject a pharmaceutically effective amount of: (a) cefepime or a pharmaceutically acceptable salt thereof, (b) sulbactam or a pharmaceutically acceptable salt thereof, and (c) trans-7-oxo-6-(sulphooxy)-1,6-diazabicyclo-[3.2.1]-octane-2-carboxamide or a pharmaceutically acceptable salt thereof.

29. A method for treating a bacterial infection in a subject, said method comprising administering to said subject a pharmaceutically effective amount of: (a) cefpirome or a pharmaceutically acceptable salt thereof, (b) sulbactam or a pharmaceutically acceptable salt thereof, and (c) trans-7-oxo-6-(sulphooxy)-1,6-diazabicyclo-[3.2.1]-octane-2-carboxamide or a pharmaceutically acceptable salt thereof.

* * * * *